United States Patent
Song et al.

(10) Patent No.: US 11,402,524 B2
(45) Date of Patent: Aug. 2, 2022

(54) GEOMETRIC CALIBRATION OF X-RAY IMAGING SYSTEMS

(71) Applicant: Imatrex, Inc., Las Vegas, NV (US)

(72) Inventors: Samuel M. Song, Las Vegas, NV (US); Namho Kim, Las Vegas, NV (US)

(73) Assignee: Imatrex, Inc., Las Vegas, NV (US)

( * ) Notice: Subject to any disclaimer, the term of this patent is extended or adjusted under 35 U.S.C. 154(b) by 150 days.

(21) Appl. No.: 16/191,132

(22) Filed: Nov. 14, 2018

(65) Prior Publication Data

US 2019/0146106 A1   May 16, 2019

Related U.S. Application Data

(60) Provisional application No. 62/585,886, filed on Nov. 14, 2017.

(51) Int. Cl.
  *A61B 6/02*   (2006.01)
  *G01T 7/00*   (2006.01)
  *G01T 1/29*   (2006.01)

(52) U.S. Cl.
  CPC ............... *G01T 7/005* (2013.01); *A61B 6/02* (2013.01); *G01T 1/2985* (2013.01)

(58) Field of Classification Search
  CPC .......... G01T 1/2985; G01T 7/002; A61B 6/02
  See application file for complete search history.

(56) References Cited

U.S. PATENT DOCUMENTS

| | | | |
|---|---|---|---|
| 2004/0245447 A1 | 12/2004 | Karasawa | |
| 2004/0264648 A1* | 12/2004 | Claus | A61B 6/583 378/163 |
| 2012/0063568 A1 | 3/2012 | Lang et al. | |
| 2014/0126800 A1 | 5/2014 | Lang et al. | |
| 2015/0085979 A1 | 3/2015 | Zheng et al. | |

FOREIGN PATENT DOCUMENTS

JP   3964155 A   11/2002
WO   2008139167 A2   11/2008

OTHER PUBLICATIONS

International Search Report and Written Opinion for International application No. PCT/US2018/061089 dated Jan. 24, 2019 in 10 pages.

* cited by examiner

*Primary Examiner* — David P Porta
*Assistant Examiner* — Fani Polyzos Boosalis
(74) *Attorney, Agent, or Firm* — Procopio, Cory, Hargreaves & Savitch LLP

(57) ABSTRACT

An apparatus for calibrating an X-ray imaging system including: an X-ray source including a plurality of focal spots; a detector panel; and at least one planar structure including markers placed at pre-determined positions on the at least one planar structure, the at least one planar structure configured to estimate a position of the plurality of focal spots with respect to the detector panel.

6 Claims, 8 Drawing Sheets

X-ray source

Calibration Phantom

Detector

GEOMETRIC CALIBRATION OF X-RAY IMAGING SYSTEMS

CROSS-REFERENCE TO RELATED APPLICATIONS

This application claims the benefit of priority under 35 U.S.C. § 119(e) of co-pending U.S. Provisional Patent Application No. 62/585,886, filed Nov. 14, 2017, entitled "GEOMETRIC CALIBRATION OF X-RAY IMAGING SYSTEMS." The disclosure of the above-referenced application is incorporated herein by reference.

BACKGROUND

Field of the Disclosure

The present disclosure relates to X-ray imaging systems, and more specifically, to geometric calibration of the X-ray imaging systems.

Background

Three-dimensional X-ray imaging systems generally include one or more X-ray focal spot and a 2-D array of detectors mounted on a rotating gantry. Thus, an accurate reconstruction of the imaged object depends on the assumed positions of the X-ray focal spot to the detector. However, mechanical systems suffer from some form of misalignment even with a careful mechanical alignment. Accordingly, any misalignment is known to degrade the spatial resolution of the imaging system and must be calibrated.

For example, numerous proposals for the geometric alignment have been made for cone-beam Computed Tomography (CT) systems. In one case, attempts were made to calibrate with a set of beads on a rotating turntable. The X-ray projection images of beads as the gantry rotates are collected and through a series of trigonometric relations the X-ray focal spot with respect to the detector panel was estimated. In another case, a similar system using metal ball bearings where the out-plane rotation was also estimated.

SUMMARY

The present disclosure is directed to geometric calibration of the X-ray imaging systems.

In one implementation, an apparatus for calibrating an X-ray imaging system is disclosed. The apparatus includes: an X-ray source including a plurality of focal spots; a detector panel; and at least one planar structure including markers placed at pre-determined positions on the at least one planar structure, the at least one planar structure configured to estimate a position of the plurality of focal spots with respect to the detector panel.

In one implementation, the markers are made of material that can be imaged by the X-ray imaging system to be calibrated. In one implementation, the at least one planar structure is a printed circuit board (PCB). In one implementation, the markers are printed copper circles on a PCB. In one implementation, the markers are printed copper dots on a PCB. In one implementation, the X-ray imaging system outputs X-ray images of the at least one planar structure having the markers. In one implementation, the markers are detected to establish correspondences among different planar structures and different rotation angles. In one implementation, the correspondences are used to estimate the elements of a projection matrix. In one implementation, the estimated elements of the projection matrix are used to determine the position of X-ray focal spot relative to the detector panel. In one implementation, the estimated elements of the projection matrix are used to determine the orientation of the detector panel.

In another implementation, a process for calibrating an X-ray imaging system is disclosed. The method includes: placing markers at pre-determined positions on at least one planar structure; placing the at least one planar structure between an X-ray source including a plurality of focal spots and a detector panel; and estimating a position of the plurality of focal spots with respect to the detector panel.

In one implementation, the process further includes moving the at least one planar structure as it is imaged by the X-ray imaging system. In one implementation, moving the at least one planar structure includes at least one of rotating and translating the at least one planar structure as it is imaged by the X-ray imaging system. In one implementation, the process further includes outputting X-ray images of the at least one planar structure having the markers. In one implementation, the process further includes estimating the position of the plurality of focal spots with respect to the detector panel using the X-ray images of the at least one planar structures. In one implementation, the process further includes estimating the positions of the markers imaged on the detector panel using the X-ray images. In one implementation, the process further includes detecting the markers to establish correspondences among different planar structures and different rotation angles. In one implementation, the process further includes estimating the elements of a projection matrix using the correspondences. In one implementation, the process further includes determining the position of X-ray focal spot relative to the detector panel using the estimated elements of the projection matrix. In one implementation, the process further includes determining the orientation of the detector panel using the estimated elements of the projection matrix.

Other features and advantages should be apparent from the present description which illustrates, by way of example, aspects of the disclosure.

BRIEF DESCRIPTION OF THE DRAWINGS

The details of the present disclosure, both as to its structure and operation, may be gleaned in part by study of the appended drawings, in which like reference numerals refer to like parts, and in which.

DETAILED DESCRIPTION

Figure 1:
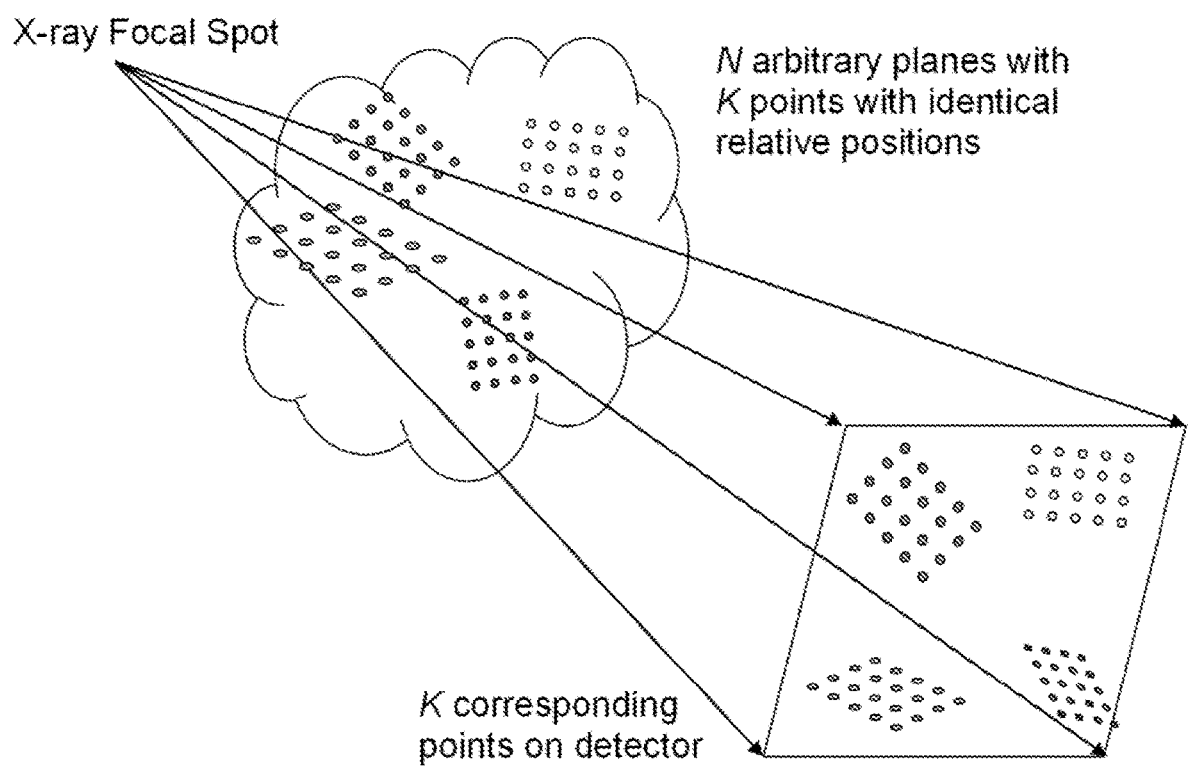
FIG. 1 is a diagram illustrating an overall concept of the present disclosure in accordance with one implementation.

As described above, past attempts at geometric alignment generally have not been satisfactory with mechanical systems. Certain implementations of the present disclosure disclose the calibration of X-ray imaging system performed with calibration phantom including planar structures with printed circuit board. The board includes a printed 2-D array of copper dots that is imaged on the detector by the X-ray source. The collection of projection images of the phantom is then processed to estimate the position of the X-ray focal spot with respect to the detector to determine the geometry of the X-ray imaging system.

After reading these descriptions, it will become apparent how to implement the disclosure in various implementations and applications. However, although various implementations of the present disclosure will be described herein, it is understood that these implementations are presented by way of example only, and not limitation. As such, this detailed description of various implementations should not be construed to limit the scope or breadth of the present disclosure.

X-ray imaging systems must be calibrated so that the accurate position of the X-ray focal spot is known with respect to the detectors on a flat or curved surface. The detectors are generally pre-arranged to be accurate to within a few tens of microns. Thus, the knowledge of the X-ray focal spot relative to the detectors is needed to determine the X-ray imaging system geometry.

The mathematical description of the geometry of an X-ray imaging system is as follows. The mathematical model shown below adapts the notations used in Computer Vision literatures to the X-ray imaging system. The projection matrix P projects the 3-D world coordinate $X=[X_1,X_2,X_3,1]^T$ to and 2-D world coordinate $x=[x_1,x_2,1]^T$ as follows:

$x=PX.$

Note that this representation is in the projective space, i.e., $X \in \mathbb{P}^3 = \mathbb{R}^4 - [0, 0, 0]^T$ and $x \in \mathbb{P}^2 = \mathbb{R}^3 - [0, 0, 0]^T$, where $\mathbb{R}$ is the real line and the equality is taken in the sense of equivalence class. The projection matrix P can be shown to be decomposed as $P=A[R t]X,$ where R and t are 3×3 rotation matrix and 3×1 translation vector, respectively, and $$A = \begin{bmatrix} \alpha & \gamma & u_0 \\ 0 & \beta & v_0 \\ 0 & 0 & 1 \end{bmatrix}.$$

The above matrix includes elements that are intrinsic parameters of the X-ray imaging system. The parameters $(u_0, v_0)$ are the locations of the principal axis from the X-ray focal spot that crosses the detector panel orthogonally, $(\alpha, \beta)$ are scale factors (in the $x_1$ and $x_2$ coordinates, respectively), and $\gamma$ is the skew parameter for the detector panel. Since the detector panels are constructed with high precision semiconductor processing, parameter $(\alpha, \beta, \gamma)=(1,1,0)$. In the present disclosure, the parameters $(\alpha, \beta, \gamma)$ are estimated.

Initially, the following symmetric matrix is defined:

$$B \equiv \begin{bmatrix} B_{11} & B_{12} & B_{13} \\ B_{12} & B_{22} & B_{23} \\ B_{13} & B_{23} & B_{33} \end{bmatrix} \equiv A^{-T}A^{-1} =$$

$$\begin{bmatrix} \frac{1}{\alpha^2} & -\frac{\gamma}{\alpha^2 \beta} & \frac{v_0\gamma - u_0\beta}{\alpha^2 \beta} \\ -\frac{\gamma}{\alpha^2 \beta} & -\frac{\gamma^2}{\alpha^2 \beta} + \frac{1}{\beta^2} & -\frac{\gamma(v_0\gamma - u_0\beta)}{\alpha^2 \beta^2} - \frac{v_0}{\beta^2} \\ \frac{v_0\gamma - u_0\beta}{\alpha^2 \beta} & -\frac{\gamma(v_0\gamma - u_0\beta)}{\alpha^2 \beta^2} - \frac{v_0}{\beta^2} & \frac{(v_0\gamma - u_0\beta)^2}{\alpha^2 \beta^2} + \frac{v_0^2}{\beta^2} + 1 \end{bmatrix}.$$

Then, the below vector is formed $b=[B_{11},B_{12},B_{22},B_{13},B_{23},B_{33}]^T.$ Further, 3×3 matrix $H=[h_1, h_2, h_3]$ whose columns are $h_1, h_2, h_3$ is defined as follows:

$H=[h_1,h_2,h_3]=\lambda A[r_1,r_2,t].$

Thus, it can be shown that $$\begin{bmatrix} v_{12}^T \\ (v_{11} - v_{22})^T \end{bmatrix} b = 0,$$

where $v_{ij}=+[h_{i1}h_{j1},h_{i1}h_{j2}+h_{i2}h_{j1},j_{i2}h_{j2},h_{i3}h_{j1}+h_{i1}h_{j3},h_{i3}h_{j2}+h_{i2}h_{j3},h_{i3}h_{j3}].$ As the above can be constructed from one image of the calibration phantom, upon stacking n measurements, following is true:

$Vb=0,$ where V is a 2n×6 matrix. The null-space of V is as follows:

$b=[B_{11},B_{12},B_{22},B_{13},B_{23},B_{33}]^T.$

Then, intrinsic parameters can be determined by $v_0=(B_{11}B_{13}-B_{11}B_{23})/(B_{11}B_{22}-B^2_{12}),$ $\lambda=B_{33}-[B^2_{13}+v_0(B_{12}B_{13}-B_{11}B_{23})]/B_{11},$ $\alpha=\sqrt{\lambda/B_{11}},$ $\beta=\sqrt{\lambda B_{11}/(B_{11}B_{22}-B^2_{12})},$ $\gamma=B_{12}\alpha^2\beta/\lambda,$ $u_0=\gamma v_0/\alpha - B_{13}\alpha^2/\lambda.$ The extrinsic parameters are determined by $r_1=\lambda A^{-1}h_1,$ $r_2=\lambda A^{-1}h_2,$ $r_3 = r_1 \times r_2,$ $t = \lambda A^{-1} h_3.$ As the absolute locations of the copper dots, i.e., X, are known, the relative scale factor can be computed, which is then used to determine the distance f from the X-ray focal spot to the detector panel.

FIG. 1 is a diagram illustrating an overall concept of the present disclosure in accordance with one implementation. The X-ray source images a known pattern (or dots) in a planar configuration. The 2-D planar structure including 2-D array of circles (or dots) can be fabricated using standard Printed Circuit Board (PCB) technique. When the planar structures are placed between the X-ray source (focal spot) and the detector plane, the structure is imaged on the detector by the impinging X-ray as shown.

Figure 2:
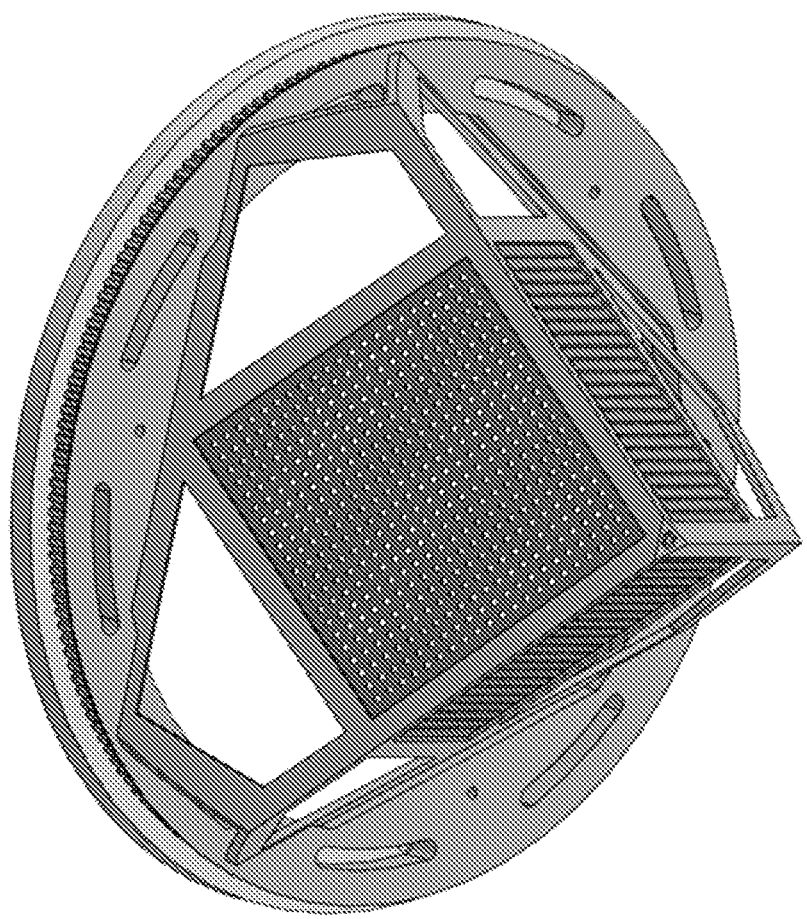
FIG. 2 is an illustration of a calibration phantom including three PCBs with printed copper dots in accordance with one implementation of the present disclosure.

FIG. 2 is an illustration of a calibration phantom including three PCBs with printed copper dots in accordance with one implementation of the present disclosure.

Figure 3:
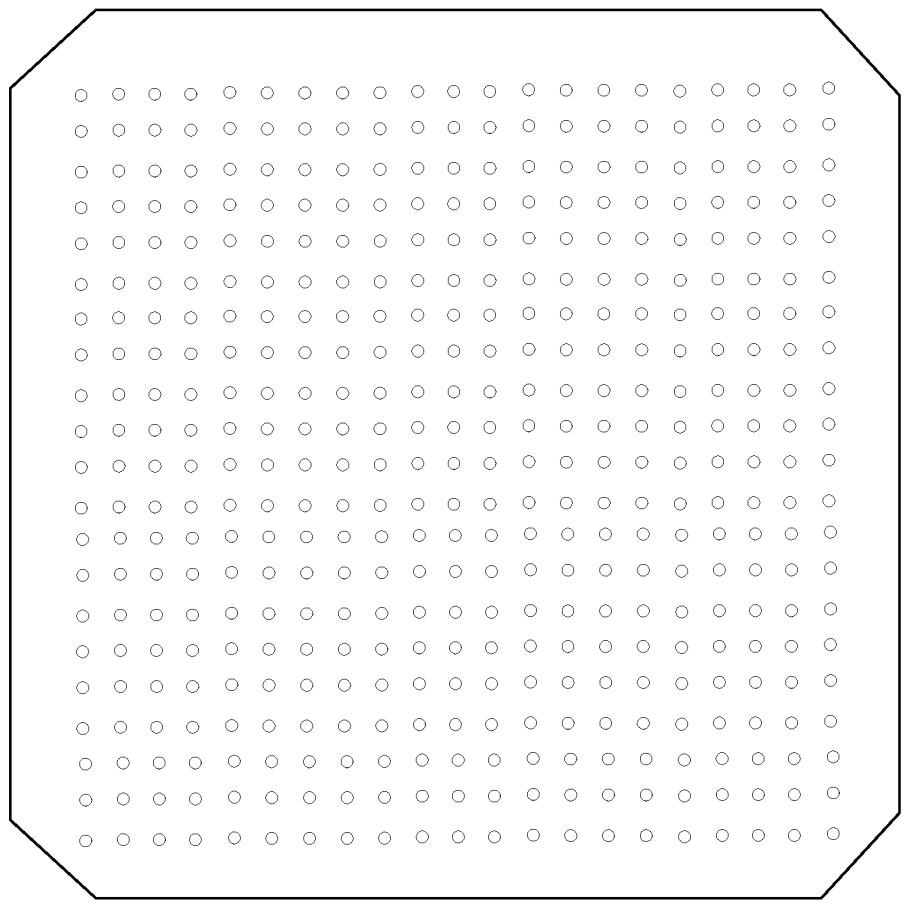
FIG. 3 is a photograph of one PCB with printed copper dots in accordance with one implementation of the present disclosure.

FIG. 3 is a photograph of one PCB with printed copper dots in accordance with one implementation of the present disclosure.

Figure 4:
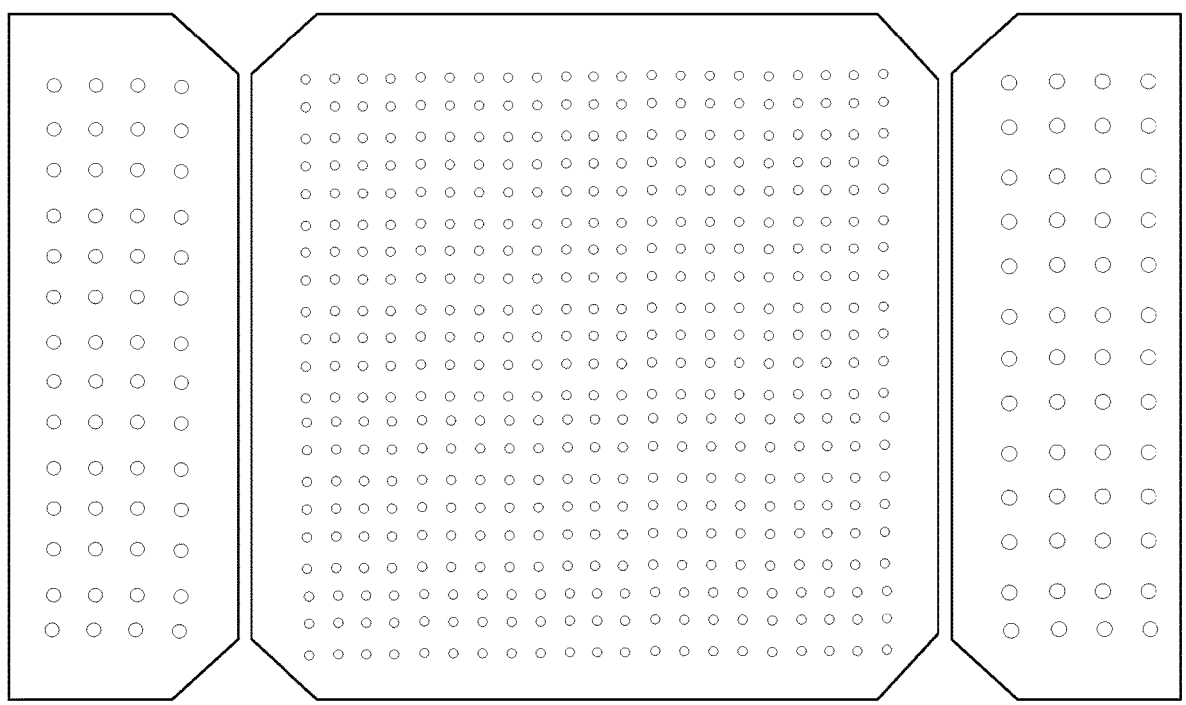
FIG. 4 is an image of the PCB with several different sizes of copper dots: 2 mm, 1 mm, 3 mm (from left to right) in accordance with one implementation of the present disclosure.

FIG. 4 is an image of the PCB with several different sizes of copper dots: 2 mm, 1 mm, 3 mm (from left to right) in accordance with one implementation of the present disclosure.

Figure 5:
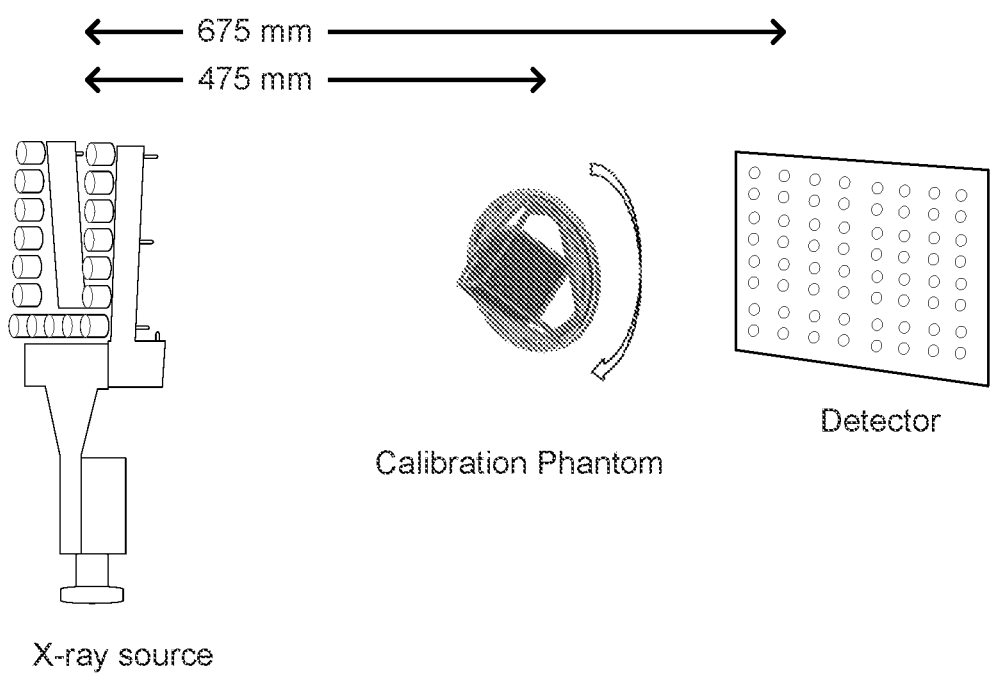
FIG. 5 is a configuration of the set-up with X-ray source at Z=0, the calibration phantom at Z=475 mm, and a planar detector panel at Z=675 mm with the X-ray source including 19 X-ray focal spots that will be active one at a time.

FIG. 5 shows an instance of X-ray imaging system that includes 19 X-ray focal spots and a detector panel in accordance with one implementation of the present disclosure. The objective is to estimate the position of 19 X-ray focal spots with respect to the detector panel. Here, it suffices to estimate the position of each focal spots by determining the minimum distance from the detector to the focal spot. As the minimum distance occurs on the line orthogonal to the detector, the position on the detector where the orthogonal line intersects the detector is sufficient.

Using the distances and the configuration shown in FIG. 5, projection images were obtained on the detector. The detector was of the size 397.3×298.0 mm² with 2048×1536 pixels. The Gaussian noise was added to the estimated position on the detector. As the data were generated with simulation, the precise locations of the 19 focal spots are known and can be used as the ground truth. We take 19 projection images of the calibration phantom. The calibration phantom is then rotated about the Z-axis (the axis from X-ray source to the detector). Then another set of 19 projection images. The process is repeated N times. Since each phantom position provides three projection images (per X-ray focal spot), there are 3N projection images for every X-ray focal spot. The 3N projection images are used to determine the position of the focal spot with respect to the detector.

In particular, FIG. 5 is a configuration of the set-up with X-ray source at Z=0, the calibration phantom at Z=475 mm, and a planar detector panel at Z=675 mm with the X-ray source including 19 X-ray focal spots that will be active one at a time. The PCB was of 10×10 cm² with 21×21 printed copper dots.

Figure 6:
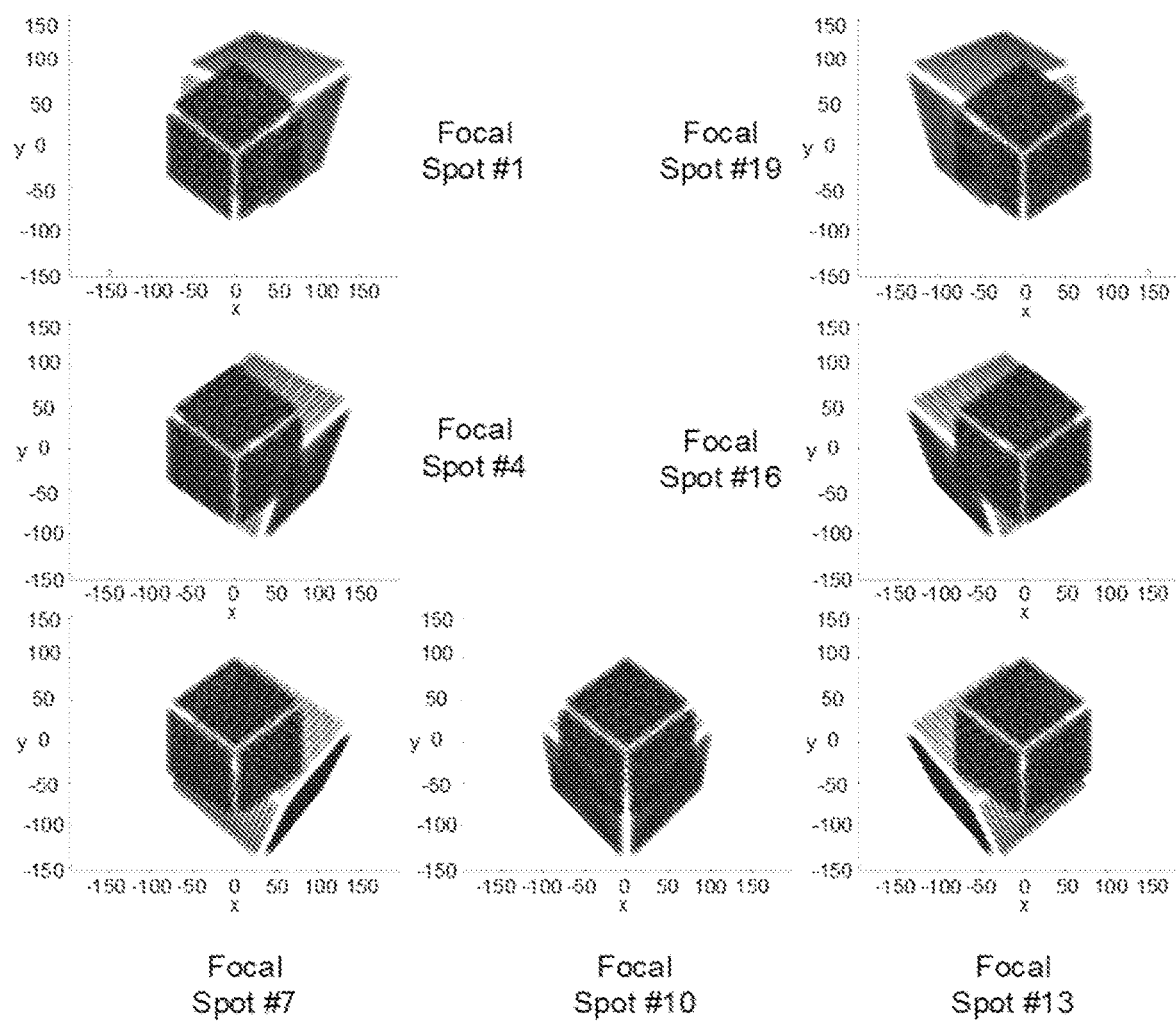
FIG. 6 shows the copper dots of the 3-D phantom (smaller cube) and the imaged copper dots on the planar detector panel for the focal spots #1, #4, #7, #10, #13, #16 and #19.

FIG. 6 shows the copper dots of the 3-D phantom (smaller cube) and the imaged copper dots on the planar detector panel. The images are shown for the focal spots #1, #4, #7, #10, #13, #16 and #19.

Figure 7A:
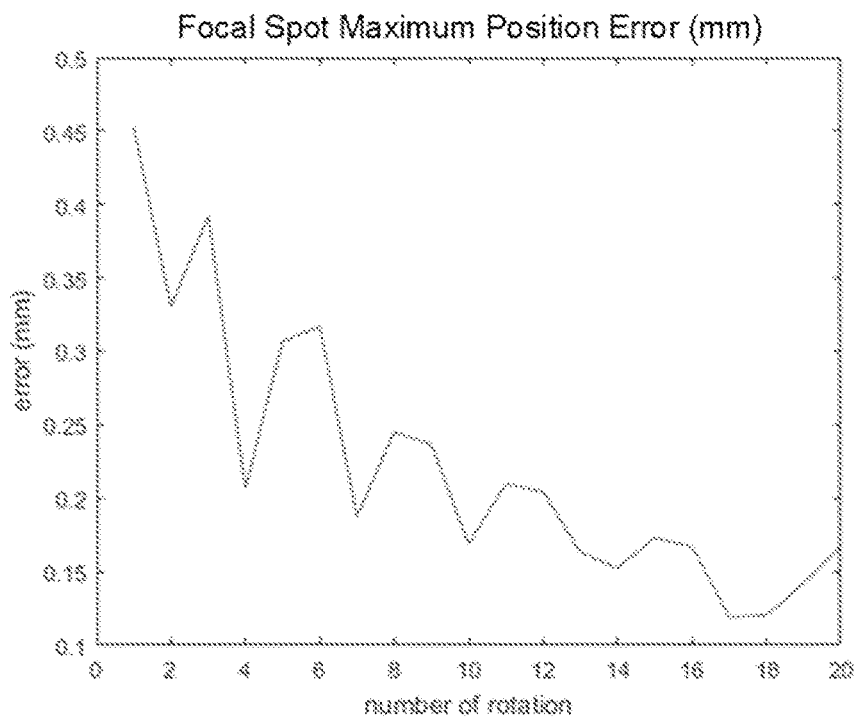
FIG. 7A is a graph showing the X-ray focal spot maximum position error as a function of number of rotations of the calibration phantom.
Figure 7B:
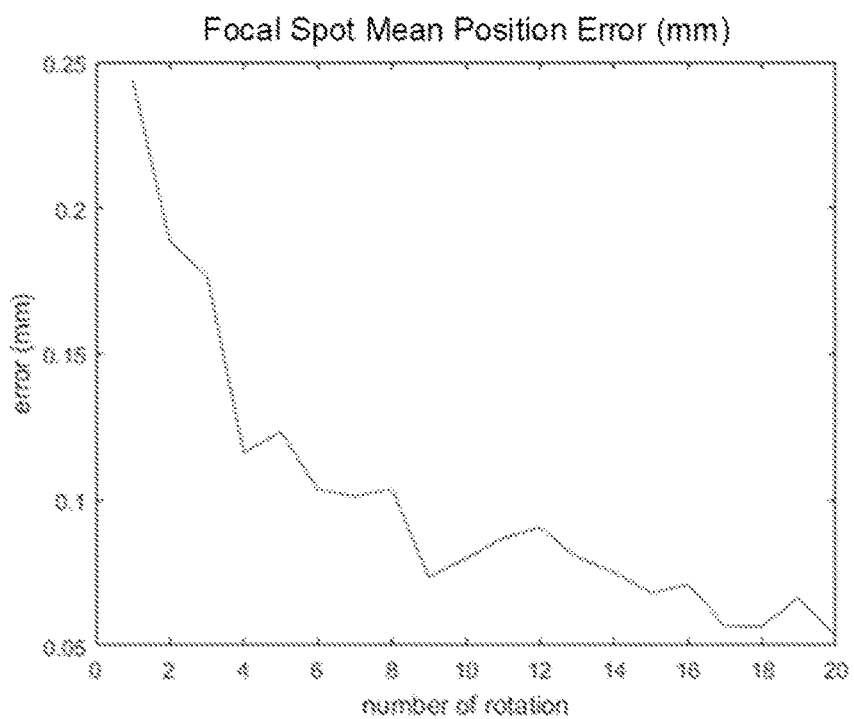
FIG. 7B is a graph showing the X-ray focal spot mean position error as a function of number of rotations of the calibration phantom.

FIGS. 7A and 7B show the results where the X-ray focal spot position error is shown as a function of the number of rotations of the calibration phantom. FIG. 7A is a graph showing the X-ray focal spot maximum position error as a function of number of rotations of the calibration phantom.

FIG. 7B is a graph showing the X-ray focal spot mean position error as a function of number of rotations of the calibration phantom.

It is shown that as the number of rotations (or projection images of the calibration phantom) increases, the error decreases. The maximum focal spot position error plot (FIG. 7A) shows that all positions have been estimated to within 150 microns. The mean target position error plot (FIG. 7B) shows that the average position error is about 50 microns.

Figure 8:
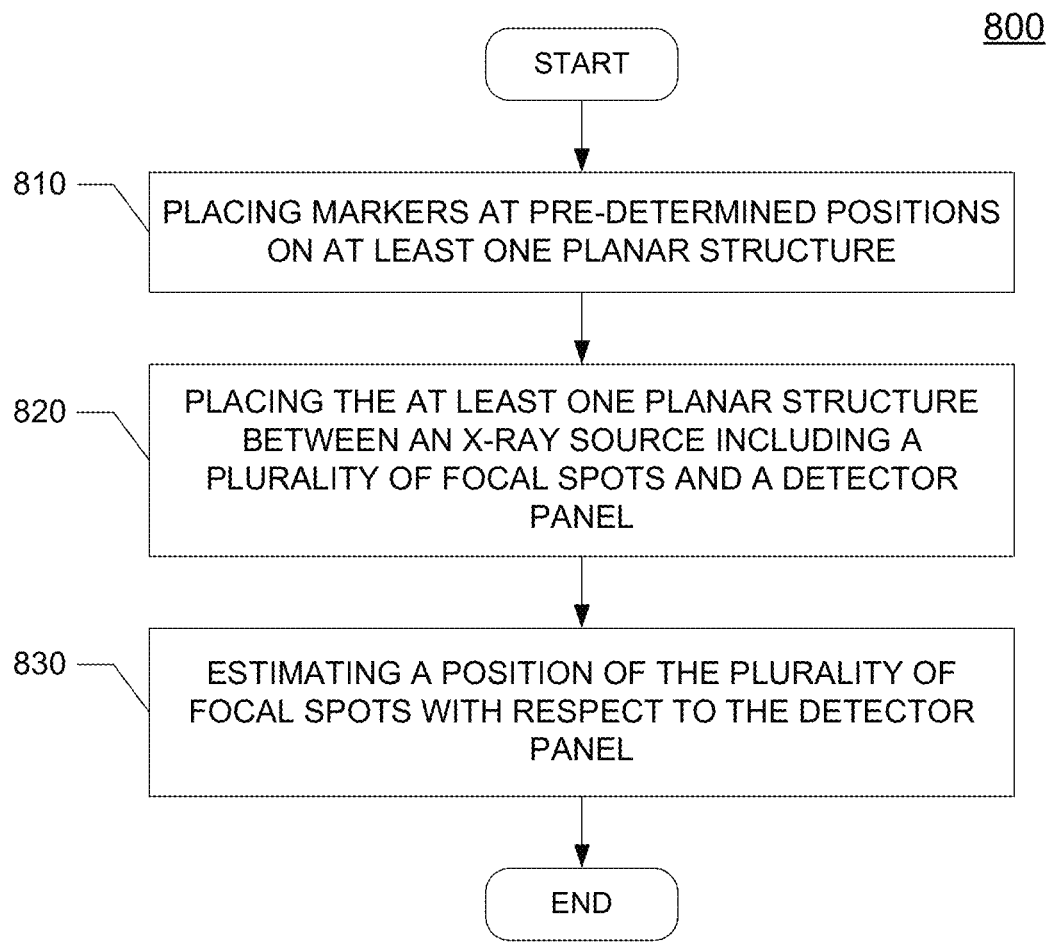
FIG. 8 is a flow diagram illustrating a process 800 for calibrating an X-ray imaging system in accordance with one implementation of the present disclosure.

FIG. 8 is a flow diagram illustrating a process 800 for calibrating an X-ray imaging system in accordance with one implementation of the present disclosure. Initially, the markers are placed at pre-determined positions, at box 810, on at least one planar structure. Then, at box 820, the at least one planar structure is placed between an X-ray source including a plurality of focal spots and a detector panel. Finally, at box 830, a position of the plurality of focal spots with respect to the detector panel is estimated.

In one implementation, the process further includes moving the at least one planar structure as it is imaged by the X-ray imaging system. In one implementation, moving the at least one planar structure includes at least one of rotating and translating the at least one planar structure as it is imaged by the X-ray imaging system. In one implementation, the process further includes outputting X-ray images of the at least one planar structure having the markers. In one implementation, the process further includes estimating the position of the plurality of focal spots with respect to the detector panel using the X-ray images of the at least one planar structures. In one implementation, the process further includes estimating the positions of the markers imaged on the detector panel using the X-ray images. In one implementation, the process further includes detecting the markers to establish correspondences among different planar structures and different rotation angles. In one implementation, the process further includes estimating the elements of a projection matrix using the correspondences. In one implementation, the process further includes determining the position of X-ray focal spot relative to the detector panel using the estimated elements of the projection matrix. In one implementation, the process further includes determining the orientation of the detector panel using the estimated elements of the projection matrix.

Various modifications to these implementations will be readily apparent to those skilled in the art, and the generic principles described herein can be applied to other implementations without departing from the spirit or scope of the disclosure. Accordingly, the techniques are not limited to the specific examples described above. Thus, it is to be understood that the description and drawings presented herein represent a presently possible implementation of the disclosure and are therefore representative of the subject matter that is broadly contemplated by the present disclosure. It is further understood that the scope of the present disclosure fully encompasses other implementations that may become obvious to those skilled in the art and that the scope of the present disclosure is accordingly limited by nothing other than the appended claims.

The invention claimed is:

1. A method for calibrating an X-ray imaging system using a calibration phantom, the method comprising:
    placing at least three markers at pre-determined positions on the calibration phantom including at least one planar structure with a plurality of printed circuit boards,
    wherein each of the plurality of printed circuit boards includes a printed 2-D array of copper dots that is imaged on the detector;

placing the at least one planar structure between an X-ray source including a plurality of focal spots and a detector panel;

estimating a position of each focal spot of the plurality of focal spots with respect to the detector panel by determining a minimum distance from the detector panel to each focal spot.

2. The method of claim 1, further comprising moving the at least one planar structure as it is imaged by the X-ray imaging system.

3. The method of claim 2, wherein moving the at least one planar structure includes at least one of rotating and translating the at least one planar structure as it is imaged by the X-ray imaging system.

4. The method of claim 1, further comprising outputting X-ray images of the at least one planar structure having the markers.

5. The method of claim 4, further comprising estimating the position of the plurality of focal spots with respect to the detector panel using the X-ray images of the at least one planar structure.

6. The method of claim 4, further comprising estimating the positions of the markers imaged on the detector panel using the X-ray images.

\* \* \* \* \*